(12) United States Patent
Joyner et al.

(10) Patent No.: US 11,468,968 B2
(45) Date of Patent: Oct. 11, 2022

(54) SYSTEMS AND METHODS FOR IDENTIFYING SOMATIC MUTATIONS

(71) Applicant: LIFE TECHNOLOGIES CORPORATION, Carlsbad, CA (US)

(72) Inventors: Alexander Joyner, San Francisco, CA (US); Fiona Hyland, San Mateo, CA (US); Heinz Breu, Palo Alto, CA (US)

(73) Assignee: Life Technologies Corporation, Carlsbad, CA (US)

( * ) Notice: Subject to any disclaimer, the term of this patent is extended or adjusted under 35 U.S.C. 154(b) by 495 days.

(21) Appl. No.: 16/434,709

(22) Filed: Jun. 7, 2019

(65) Prior Publication Data

US 2019/0371431 A1 Dec. 5, 2019

Related U.S. Application Data

(60) Continuation of application No. 15/295,114, filed on Oct. 17, 2016, now abandoned, which is a division of application No. 13/790,713, filed on Mar. 8, 2013, now abandoned.

(60) Provisional application No. 61/621,941, filed on Apr. 9, 2012.

(51) Int. Cl.
*G16B 20/20* (2019.01)
*G16B 30/00* (2019.01)
*G16B 30/10* (2019.01)

(52) U.S. Cl.
CPC .............. *G16B 20/20* (2019.02); *G16B 30/00* (2019.02); *G16B 30/10* (2019.02)

(58) Field of Classification Search
CPC ......... G16B 20/20; G16B 30/10; G16B 30/00
See application file for complete search history.

(56) References Cited

U.S. PATENT DOCUMENTS

| | | |
|---|---|---|
| 2009/0026082 A1 | 1/2009 | Rothberg et al. |
| 2009/0127589 A1 | 5/2009 | Rothberg et al. |
| 2009/0325145 A1 | 12/2009 | Sablon et al. |
| 2010/0137143 A1 | 6/2010 | Rothberg et al. |
| 2010/0197507 A1 | 8/2010 | Rothberg et al. |
| 2010/0300559 A1 | 12/2010 | Schultz et al. |
| 2010/0300895 A1 | 12/2010 | Nobile et al. |
| 2010/0301398 A1 | 12/2010 | Rothberg et al. |
| 2013/0091126 A1 | 4/2013 | Krishnaswami et al. |

FOREIGN PATENT DOCUMENTS

| | | |
|---|---|---|
| WO | WO-2006084131 A2 | 8/2006 |
| WO | WO-2012044847 A1 | 4/2012 |

OTHER PUBLICATIONS

Li, H. , "A Statistical Framework for SNP Calling, Mutation Discovery, Association Mapping and Population Genetical Parameter Estimation From Sequencing Data", Bioinformatics, vol. 27, No. 21, Sep. 8, 2011, 2987-2993.

Sambrook et al., "Molecular Cloning: A Laboratory Manual", Third ed., Cold Spring Harbor Laboratory Press, Cold Spring Harbor, N.Y., 2000, cover pages and table of contents, 25 pages.

*Primary Examiner* — Jerry Lin

(57) ABSTRACT

Systems and method for identifying somatic mutations can receive first and second sequence information, determine if a variant present in the first sequencing information is also present in the second sequence information, and identify variants present in the first sequence information are somatic mutations when the variant is either not present in the second sequence information or the presence of the variant in the second sequence information is likely due to a sequencing error.

19 Claims, 6 Drawing Sheets

SYSTEMS AND METHODS FOR IDENTIFYING SOMATIC MUTATIONS

RELATED APPLICATIONS

This application is a continuation of U.S. application Ser. No. 15/295,114 filed Oct. 17, 2016, which is a division of U.S. application Ser. No. 13/790,713 filed Mar. 8, 2013, now abandoned, and claims priority to U.S. application No. 61/621,941 filed Apr. 9, 2012, which disclosures are herein incorporated by reference in their entirety.

FIELD

The present disclosure generally relates to the field of nucleic acid sequencing including systems and methods for identifying genomic variants using nucleic acid sequencing data.

INTRODUCTION

Upon completion of the Human Genome Project, one focus of the sequencing industry has shifted to finding higher throughput and/or lower cost nucleic acid sequencing technologies, sometimes referred to as "next generation" sequencing (NGS) technologies. In making sequencing higher throughput and/or less expensive, the goal is to make the technology more accessible. These goals can be reached through the use of sequencing platforms and methods that provide sample preparation for samples of significant complexity, sequencing larger numbers of samples in parallel (for example through use of barcodes and multiplex analysis), and/or processing high volumes of information efficiently and completing the analysis in a timely manner. Various methods, such as, for example, sequencing by synthesis, sequencing by hybridization, and sequencing by ligation are evolving to meet these challenges.

Ultra-high throughput nucleic acid sequencing systems incorporating NGS technologies typically produce a large number of short sequence reads. Sequence processing methods should desirably assemble and/or map a large number of reads quickly and efficiently, such as to minimize use of computational resources. For example, data arising from sequencing of a mammalian genome can result in tens or hundreds of millions of reads that typically need to be assembled before they can be further analyzed to determine their biological, diagnostic and/or therapeutic relevance.

Exemplary applications of NGS technologies include, but are not limited to: genomic variant detection, such as insertions/deletions, copy number variations, single nucleotide polymorphisms, etc., genomic resequencing, gene expression analysis and genomic profiling.

Of particular interest are improved systems and methods for detecting somatic mutations, such as those found in cancerous tumors. For example, identification of a somatic mutation specific to a cancerous tumor and not found in normal tissue can lead to insights into the development of cancer, aid in the discovery of new cancer treatments, or guide the selection of appropriate treatments for a cancer patient.

From the foregoing it will be appreciated that a need exists for systems and methods that can identify somatic mutations using nucleic acid sequencing data.

DRAWINGS

For a more complete understanding of the principles disclosed herein, and the advantages thereof, reference is now made to the following descriptions taken in conjunction with the accompanying drawings, in which.

Figure 1:
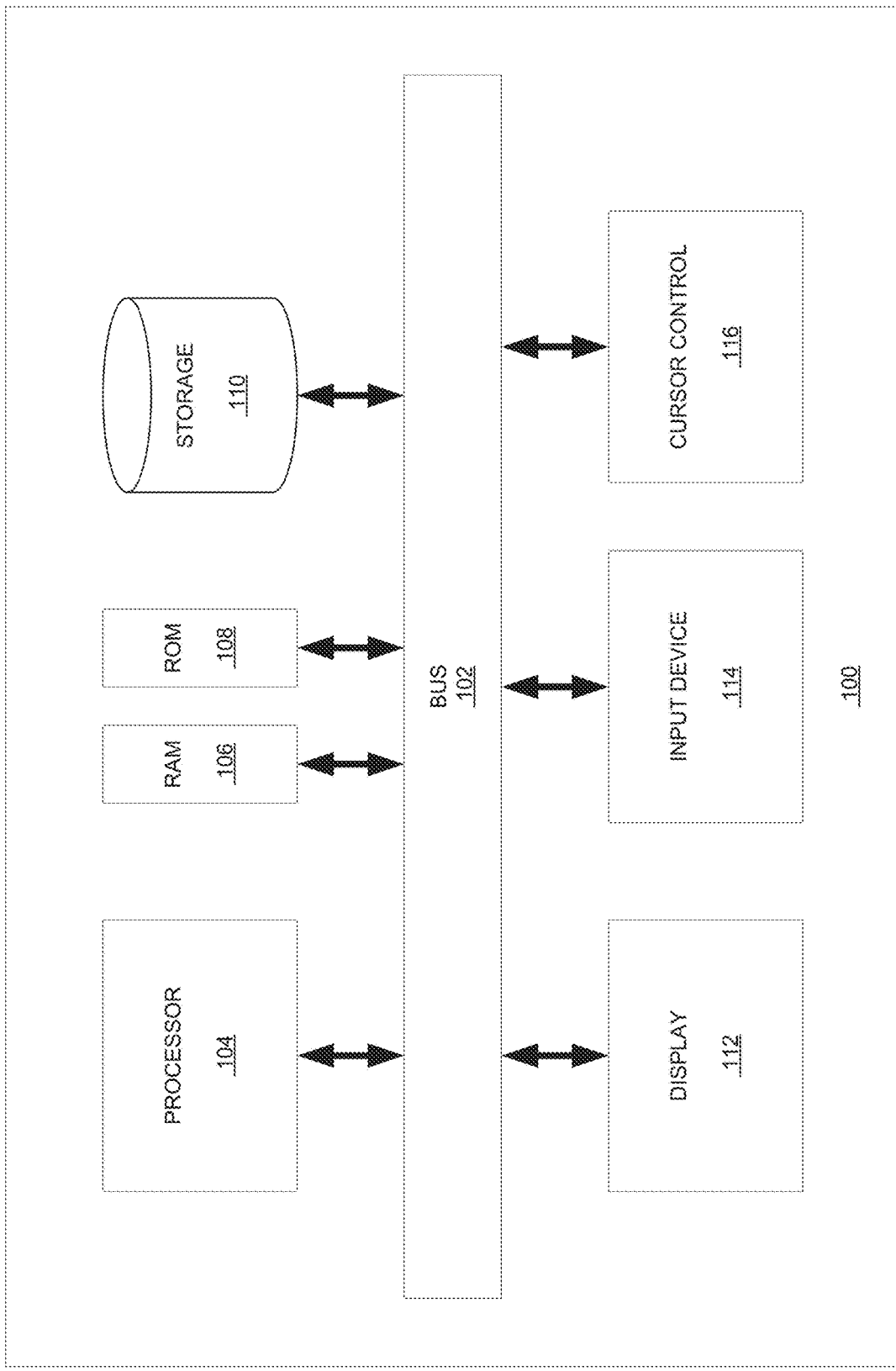
FIG. 1 is a block diagram that illustrates an exemplary computer system, in accordance with various embodiments.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DESCRIPTION OF VARIOUS EMBODIMENTS

The section headings used herein are for organizational purposes only and are not to be construed as limiting the described subject matter in any way.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and internet web pages are expressly incorporated by reference in their entirety for any purpose. Unless described otherwise, all technical and scientific terms used herein have a meaning as is commonly understood by one of ordinary skill in the art to which the various embodiments described herein belongs.

It will be appreciated that there is an implied "about" prior to the temperatures, concentrations, times, number of bases, coverage, etc. discussed in the present teachings, such that slight and insubstantial deviations are within the scope of the present teachings. In this application, the use of the singular includes the plural unless specifically stated otherwise. Also, the use of "comprise", "comprises", "comprising", "contain", "contains", "containing", "include", "includes", and "including" are not intended to be limiting. It is to be understood that both the foregoing general description and the following detailed description are exemplary and explanatory only and are not restrictive of the present teachings.

As used herein, "a" or "an" also may refer to "at least one" or "one or more." Also, the use of "or" is inclusive, such that the phrase "A or B" is true when "A" is true, "B" is true, or both "A" and "B" are true.

Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art. Standard techniques are used, for example, for nucleic acid purification and preparation, chemical analysis, recombinant nucleic acid, and oligonucleotide synthesis. Enzymatic reactions and purification techniques are performed according to manufacturer's specifications or as commonly accomplished in the art or as described herein. The techniques and procedures described herein are generally performed according to conventional methods well known in the art and as described in various general and more specific references that are cited and discussed throughout the instant specification. See, e.g., Sambrook et al., *Molecular Cloning: A Laboratory Manual* (Third ed., Cold Spring Harbor Laboratory Press, Cold Spring Harbor, N.Y. 2000). The nomenclatures utilized in connection with, and the laboratory procedures and techniques described herein are those well known and commonly used in the art.

A "system" sets forth a set of components, real or abstract, comprising a whole where each component interacts with or is related to at least one other component within the whole.

A "biomolecule" may refer to any molecule that is produced by a biological organism, including large polymeric molecules such as proteins, polysaccharides, lipids, and nucleic acids (DNA and RNA) as well as small molecules such as primary metabolites, secondary metabolites, and other natural products.

The phrase "next generation sequencing" or NGS refers to sequencing technologies having increased throughput as compared to traditional Sanger- and capillary electrophoresis-based approaches, for example with the ability to generate hundreds of thousands of relatively small sequence reads at a time. Some examples of next generation sequencing techniques include, but are not limited to, sequencing by synthesis, sequencing by ligation, and sequencing by hybridization. More specifically, the Personal Genome Machine (PGM) of Life Technologies Corp. provides massively parallel sequencing with enhanced accuracy. The PGM System and associated workflows, protocols, chemistries, etc. are described in more detail in U.S. Patent Application Publication No. 2009/0127589 and No. 2009/0026082, the entirety of each of these applications being incorporated herein by reference.

The phrase "sequencing run" refers to any step or portion of a sequencing experiment performed to determine some information relating to at least one biomolecule (e.g., nucleic acid molecule).

The phase "base space" refers to a representation of the sequence of nucleotides. The phase "flow space" refers to a representation of the incorporation event or non-incorporation event for a particular nucleotide flow. For example, flow space can be a series of zeros and ones representing a nucleotide incorporation event (a one, "1") or a non-incorporation event (a zero, "0") for that particular nucleotide flow. It should be understood that zeros and ones are convenient representations of a non-incorporation event and a nucleotide incorporation event; however, any other symbol or designation could be used alternatively to represent and/or identify these events and non-events.

DNA (deoxyribonucleic acid) is a chain of nucleotides consisting of 4 types of nucleotides; A (adenine), T (thymine), C (cytosine), and G (guanine), and that RNA (ribonucleic acid) is comprised of 4 types of nucleotides; A, U (uracil), G, and C. Certain pairs of nucleotides specifically bind to one another in a complementary fashion (called complementary base pairing). That is, adenine (A) pairs with thymine (T) (in the case of RNA, however, adenine (A) pairs with uracil (U)), and cytosine (C) pairs with guanine (G). When a first nucleic acid strand binds to a second nucleic acid strand made up of nucleotides that are complementary to those in the first strand, the two strands bind to form a double strand. As used herein, "nucleic acid sequencing data," "nucleic acid sequencing information," "nucleic acid sequence," "genomic sequence," "genetic sequence," or "fragment sequence," or "nucleic acid sequencing read" denotes any information or data that is indicative of the order of the nucleotide bases (e.g., adenine, guanine, cytosine, and thymine/uracil) in a molecule (e.g., whole genome, whole transcriptome, exome, oligonucleotide, polynucleotide, fragment, etc.) of DNA or RNA. It should be understood that the present teachings contemplate sequence information obtained using all available varieties of techniques, platforms or technologies, including, but not limited to: capillary electrophoresis, microarrays, ligation-based systems, polymerase-based systems, hybridization-based systems, direct or indirect nucleotide identification systems, pyrosequencing, ion- or pH-based detection systems, electronic signature-based systems, etc.

A "polynucleotide", "nucleic acid", or "oligonucleotide" refers to a linear polymer of nucleosides (including deoxyribonucleosides, ribonucleosides, or analogs thereof) joined by internucleosidic linkages. Typically, a polynucleotide comprises at least three nucleosides. Usually oligonucleotides range in size from a few monomeric units, e.g. 3-4, to several hundreds of monomeric units. Whenever a polynucleotide such as an oligonucleotide is represented by a sequence of letters, such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, unless otherwise noted. The letters A, C, G, and T may be used to refer to the bases themselves, to nucleosides, or to nucleotides comprising the bases, as is standard in the art.

As used herein, a "somatic variation" or "somatic mutation" can refer to a variation in genetic sequence that results from a mutation that occurs in a non-germline cell. The variation can be passed on to daughter cells through mitotic division. This can result in a group of cells having a genetic difference from the rest of the cells of an organism. Additionally, as the variation does not occur in a germline cell, the mutation may not be inherited by progeny organisms.

Computer-Implemented System

FIG. 1 is a block diagram that illustrates a computer system 100, upon which embodiments of the present teachings may be implemented. In various embodiments, computer system 100 can include a bus 102 or other communication mechanism for communicating information, and a processor 104 coupled with bus 102 for processing information. In various embodiments, computer system 100 can also include a memory 106, which can be a random access memory (RAM) or other dynamic storage device, coupled to bus 102 for determining base calls, and instructions to be executed by processor 104. Memory 106 also can be used for storing temporary variables or other intermediate information during execution of instructions to be executed by processor 104. In various embodiments, computer system 100 can further include a read only memory (ROM) 108 or other static storage device coupled to bus 102 for storing static information and instructions for processor 104. A storage device 110, such as a magnetic disk or optical disk, can be provided and coupled to bus 102 for storing information and instructions.

In various embodiments, computer system 100 can be coupled via bus 102 to a display 112, such as a cathode ray tube (CRT) or liquid crystal display (LCD), for displaying information to a computer user. An input device 114, including alphanumeric and other keys, can be coupled to bus 102 for communicating information and command selections to processor 104. Another type of user input device is a cursor control 116, such as a mouse, a trackball or cursor direction keys for communicating direction information and command selections to processor 104 and for controlling cursor movement on display 112. This input device typically has two degrees of freedom in two axes, a first axis (i.e., x) and a second axis (i.e., y), that allows the device to specify positions in a plane.

A computer system 100 can perform the present teachings. Consistent with certain implementations of the present teachings, results can be provided by computer system 100 in response to processor 104 executing one or more sequences of one or more instructions contained in memory 106. Such instructions can be read into memory 106 from another computer-readable medium, such as storage device 110. Execution of the sequences of instructions contained in memory 106 can cause processor 104 to perform the processes described herein. Alternatively hard-wired circuitry can be used in place of or in combination with software instructions to implement the present teachings. Thus implementations of the present teachings are not limited to any specific combination of hardware circuitry and software.

The term "computer-readable medium" as used herein refers to any media that participates in providing instructions to processor 104 for execution. Such a medium can take many forms, including but not limited to, non-volatile media, volatile media, and transmission media. Examples of non-volatile media can include, but are not limited to, optical or magnetic disks, such as storage device 110. Examples of volatile media can include, but are not limited to, dynamic memory, such as memory 106. Examples of transmission media can include, but are not limited to, coaxial cables, copper wire, and fiber optics, including the wires that comprise bus 102.

Common forms of non-transitory computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, or any other tangible medium from which a computer can read.

In accordance with various embodiments, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

Nucleic Acid Sequencing Platforms

Nucleic acid sequence data can be generated using various techniques, platforms or technologies, including, but not limited to: capillary electrophoresis, microarrays, ligation-based systems, polymerase-based systems, hybridization-based systems, direct or indirect nucleotide identification systems, pyrosequencing, ion- or pH-based detection systems, electronic signature-based systems, etc.

Figure 2:
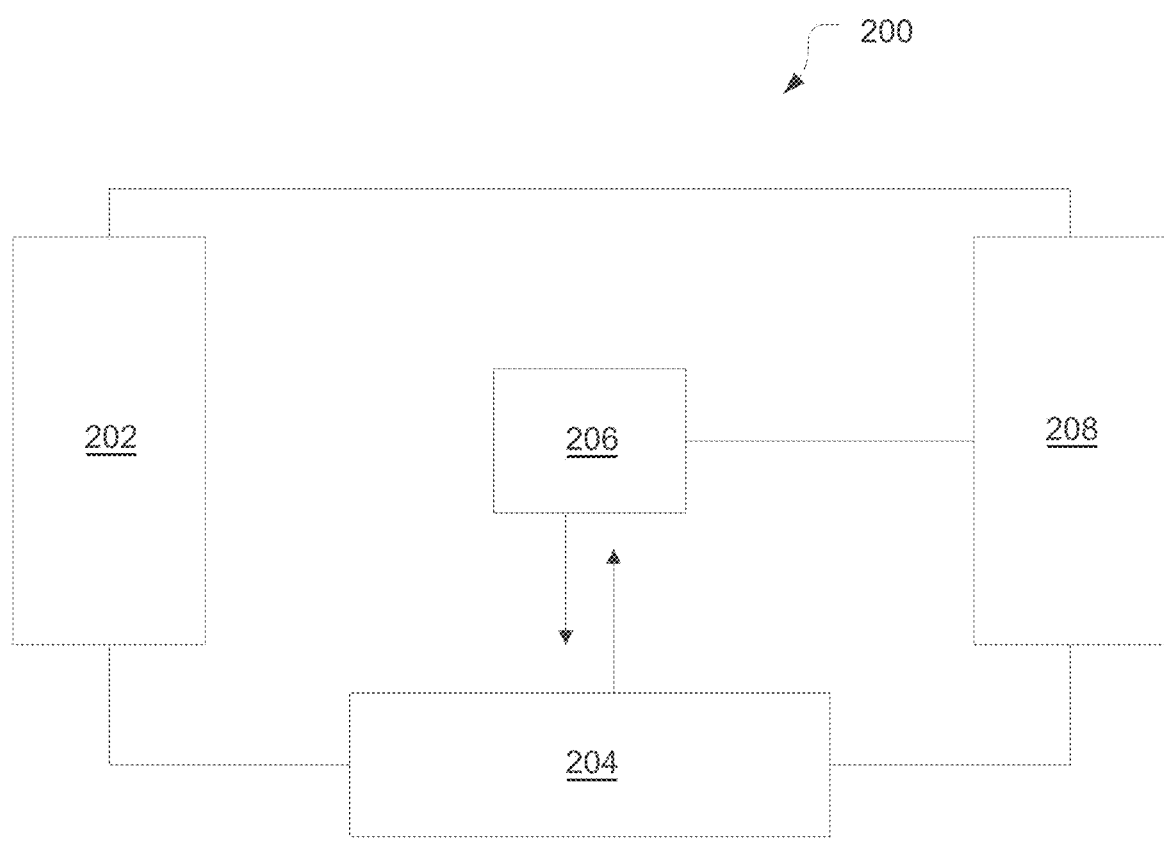
FIG. 2 is a schematic diagram of an exemplary system for reconstructing a nucleic acid sequence, in accordance with various embodiments.

Various embodiments of nucleic acid sequencing platforms, such as a nucleic acid sequencer, can include components as displayed in the block diagram of FIG. 2. According to various embodiments, sequencing instrument 200 can include a fluidic delivery and control unit 202, a sample processing unit 204, a signal detection unit 206, and a data acquisition, analysis and control unit 208. Various embodiments of instrumentation, reagents, libraries and methods used for next generation sequencing are described in U.S. Patent Application Publication No. 2009/0127589 and No. 2009/0026082 are incorporated herein by reference. Various embodiments of instrument 200 can provide for automated sequencing that can be used to gather sequence information from a plurality of sequences in parallel, such as substantially simultaneously.

In various embodiments, the fluidics delivery and control unit 202 can include reagent delivery system. The reagent delivery system can include a reagent reservoir for the storage of various reagents. The reagents can include RNA-based primers, forward/reverse DNA primers, oligonucleotide mixtures for ligation sequencing, nucleotide mixtures for sequencing-by-synthesis, optional ECC oligonucleotide mixtures, buffers, wash reagents, blocking reagent, stripping reagents, and the like. Additionally, the reagent delivery system can include a pipetting system or a continuous flow system which connects the sample processing unit with the reagent reservoir.

In various embodiments, the sample processing unit 204 can include a sample chamber, such as flow cell, a substrate, a micro-array, a multi-well tray, or the like. The sample processing unit 204 can include multiple lanes, multiple channels, multiple wells, or other means of processing multiple sample sets substantially simultaneously. Additionally, the sample processing unit can include multiple sample chambers to enable processing of multiple runs simultaneously. In particular embodiments, the system can perform signal detection on one sample chamber while substantially simultaneously processing another sample chamber. Additionally, the sample processing unit can include an automation system for moving or manipulating the sample chamber.

In various embodiments, the signal detection unit 206 can include an imaging or detection sensor. For example, the imaging or detection sensor can include a CCD, a CMOS, an ion or chemical sensor, such as an ion sensitive layer overlying a CMOS or FET, a current or voltage detector, or the like. The signal detection unit 206 can include an excitation system to cause a probe, such as a fluorescent dye, to emit a signal. The excitation system can include an illumination source, such as arc lamp, a laser, a light emitting diode (LED), or the like. In particular embodiments, the signal detection unit 206 can include optics for the transmission of light from an illumination source to the sample or from the sample to the imaging or detection sensor. Alternatively, the signal detection unit 206 may provide for electronic or non-photon based methods for detection and consequently may not include an illumination source. In various embodiments, electronic-based signal detection may occur when a detectable signal or species is produced during a sequencing reaction. For example, a signal can be produced by the interaction of a released byproduct or moiety, such as a released ion, such as a hydrogen ion, interacting with an ion or chemical sensitive layer. In other embodiments a detectable signal may arise as a result of an enzymatic cascade such as used in pyrosequencing (see, for example, U.S. Patent Application Publication No. 2009/0325145, the entirety of which being incorporated herein by reference) where pyrophosphate is generated through base incorporation by a polymerase which further reacts with ATP sulfurylase to generate ATP in the presence of adenosine 5' phosphosulfate wherein the ATP generated may be consumed in a luciferase mediated reaction to generate a chemiluminescent signal. In another example, changes in an electrical current can be detected as a nucleic acid passes through a nanopore without the need for an illumination source.

In various embodiments, a data acquisition analysis and control unit 208 can monitor various system parameters. The system parameters can include temperature of various portions of instrument 200, such as sample processing unit or reagent reservoirs, volumes of various reagents, the status of various system subcomponents, such as a manipulator, a stepper motor, a pump, or the like, or any combination thereof.

It will be appreciated by one skilled in the art that various embodiments of instrument 200 can be used to practice variety of sequencing methods including ligation-based methods, sequencing by synthesis, single molecule methods, nanopore sequencing, and other sequencing techniques.

In various embodiments, the sequencing instrument 200 can determine the sequence of a nucleic acid, such as a polynucleotide or an oligonucleotide. The nucleic acid can include DNA or RNA, and can be single stranded, such as ssDNA and RNA, or double stranded, such as dsDNA or a RNA/cDNA pair. In various embodiments, the nucleic acid can include or be derived from a fragment library, a mate pair library, a ChIP fragment, or the like. In particular embodiments, the sequencing instrument 200 can obtain the sequence information from a single nucleic acid molecule or from a group of substantially identical nucleic acid molecules.

In various embodiments, sequencing instrument 200 can output nucleic acid sequencing read data in a variety of different output data file types/formats, including, but not limited to: *.fasta, *.csfasta, *seq.txt, *qseq.txt, *.fastq, *.sff, *prb.txt, *.sms, *srs and/or *.qv.

Adaptor-Joining Methods:

In some embodiments, the present teachings are directed to methods for preparing a library of polynucleotide constructs which can include an adaptor-joining step. In some embodiments, a plurality of polynucleotide fragments can include at least two polynucleotide fragments that are joined to one or more nucleic acid adaptors by hybridization (e.g., with or without a primer extension reaction) or enzymatic ligation (e.g., a ligase reaction) to generate adaptor-fragment constructs. In some embodiments, one end or both ends of polynucleotide fragments can be joined to at least one type of adaptor. One or both ends of a polynucleotide fragment can be joined to at least one nucleic acid adaptor, including barcoded adaptors, sequencing primer adaptors, amplification primer adaptors, universal adaptors, blocking oligonucleotide adaptors and/or others.

In some embodiments, an adaptor can include nucleotide sequences that are complementary to sequencing primers (e.g., P1, P2 and/or A), amplification primers, universal sequences and/or barcode sequences. For example, released mate pair constructs can be joined at each end to a different sequencing adaptor to prepare a nucleic acid library for sequencing with SOLID' sequencing reactions (WO 2006/084131) or sequencing with ion-sensitive sequencing reactions (e.g., Ion Torrent PGM™ and Proton™ sequencers from Life Technologies Corporation, see for example U.S. Patent Publication Nos. 2010/0301398, 2010/0300895, 2010/0300559, 2010/0197507, 2010/0137143, 2009/0127589; and 2009/0026082, which are incorporated by reference in their entireties).

Barcoded Adaptor Sequences

In some embodiments, the present teachings are directed to methods for preparing a library of polynucleotide constructs which can include joining at least one end of a plurality of polynucleotide fragments to an adaptor having a barcode sequence. A barcode sequence can be a selected sequence of nucleotide bases (e.g. adenine, guanine, cytosine, thymine, uracil, inosine, or analogs thereof) in the polynucleotide strand that serves to identify the polynucleotide strand and/or distinguish it from other polynucleotide strands (e.g. those containing a different target sequence of interest). In some embodiments, a barcode adaptor can include a unique identification sequence (e.g., barcode sequence). A barcode sequence can be used for various purposes, such as tracking, sorting, and/or identifying the samples.

Because different barcode sequences can be associated with different polynucleotide strands, these barcode sequences may be useful in multiplexed sequencing of different samples. In some embodiments, a barcode adaptor can be used for constructing multiplex nucleic acid libraries. In some embodiments, one or more barcode sequences can allow identification of a particular adaptor among a mixture of different adaptors having different barcodes sequences. For example, a mixture can include 2, 3, 4, 5, 6, 7-10, 10-50, 50-100, 100-200, 200-500, 500-1000, or more different adaptors having unique barcode sequences. Examples of various adaptors having barcode sequences can be found in PCT/US2011/054053 which is incorporated by reference in its entirety.

In various high throughput DNA sequencing technologies (such as sequencing-by-synthesis) it is desirable to permit sequencing of different samples that are pooled together for simultaneous analysis (sometimes referred to as multiplexed sequencing).

When carrying out multiplexed sequencing, it is generally desirable to identify the origin of each sample, and this may require that the sequencing data be deconvolved for each sample. In particular, it can be desirable to uniquely identify the source of the sequence data derived from a multiplex sample (for example, to identify a particular nucleic acid species associated with different sample populations). One approach to facilitate sample identification is the use of unique nucleic acid identifier sequences (barcode adaptors) that are embedded within the sample construct so that sequencing data can be correctly identified or associated with its source sample.

System and Methods for Identifying Sequence Variation

Figure 3:
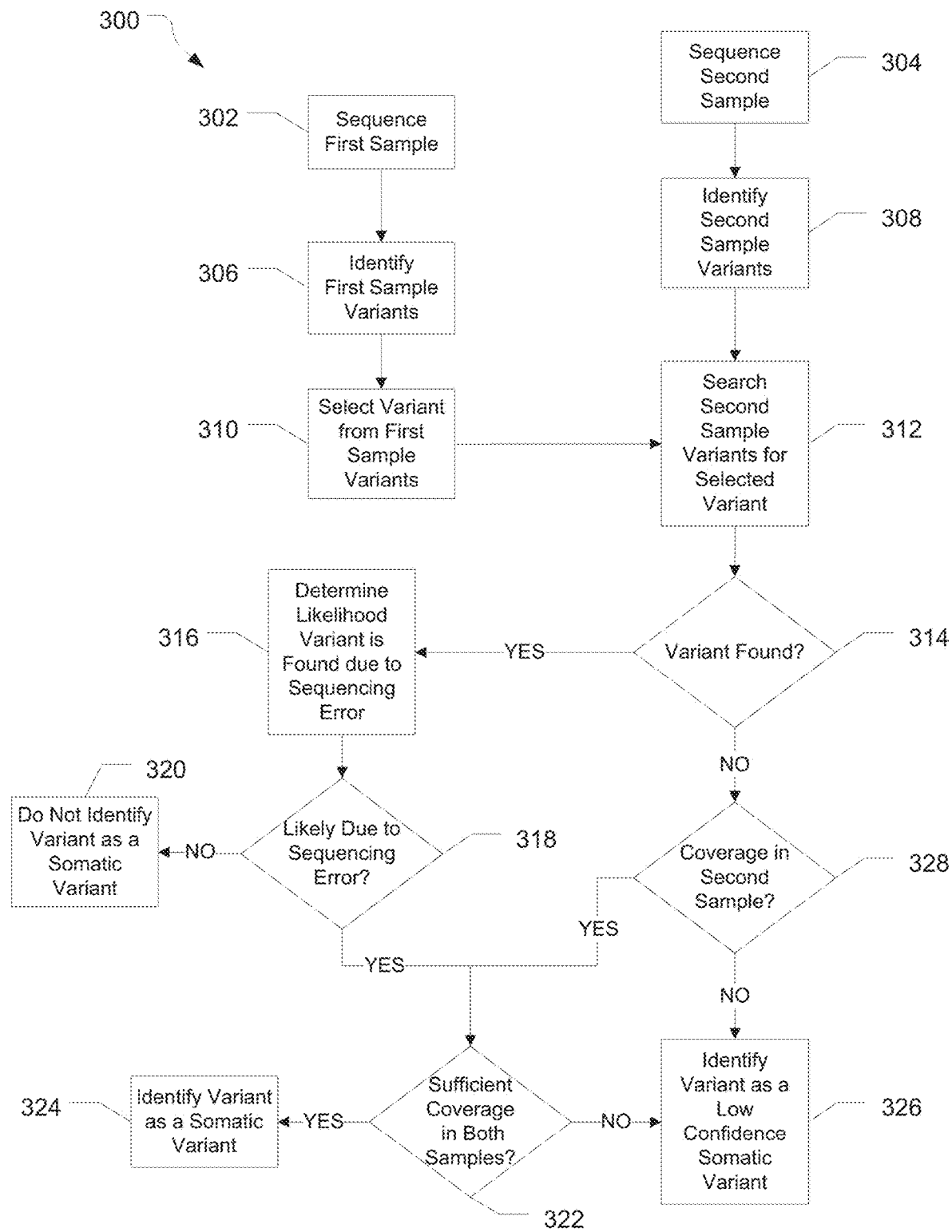
FIG. 3 is a flow diagram illustrating an exemplary method of identifying somatic mutations, in accordance with various embodiments.

FIG. 3 is an exemplary flow diagram showing a method 300 for identifying somatic variants in nucleic acid sequence reads, in accordance with various embodiments. In an exemplary embodiment, genetic information from two samples, such as from tumor biopsy and from normal tissue, can be compared in order to identify somatic variants that are unique to the tumor tissue.

At 302, sequence information can be obtained from the first sample. In exemplary embodiments, the first sample can be tissue from a tumor, such as from a tumor biopsy. The sequence information can be obtained, for example, by isolating and sequencing DNA or RNA from the first sample. In various embodiments, an exome, a genome, or portions thereof can be sequenced. In particular embodiments, specific portions of a genome or exome can be sequenced by selecting for or selectively amplifying the specific portions.

Similarly, at 304, sequence information can be from the second sample. In exemplary embodiments, the second sample can be normal or non-tumorous tissue, such as from a biopsy from another site distant from the tumor or a blood sample, or the like.

In various embodiments, a first set of fragments can be prepared from the first sample and a second set of fragments can be prepared from the second sample. The fragments can be prepared such as by mechanical sheering of the polynucleic acids, cleaving the polynucleic acids with enzymes, such as restriction endonucleases, or selective amplification of portions of the nucleic acid sequence. Barcode sequences for identification of fragments from the first and second samples can be added to the fragments. For example, a first adaptor containing a first barcode sequence can be added to the first set of fragments and a second adaptor containing a second barcode sequence can be added to the second set of fragments. The barcoded fragments of the first and second set can be combined and sequenced together, and the presence of the first or second barcode sequence in the sequence information can be used to identify sequence information from the first or second sample. By combining the samples and sequencing together, the differences in the sequencing information that can occur due to variations between sequencing runs can be controlled.

At 306, variants can be identified for the first sample. For example, the sequence information for the first sample can be mapped to a reference genome and locations where the sequence information and the reference genome differ can be identified as variants of the first sample. Various algorithms are known in the art for mapping reads to a reference genome and identifying variants.

In exemplary embodiments, the algorithms for identifying variants can be used to identify low frequency variants, such as variants that occur in fewer than 50% of the sequence reads. Significantly, tumor samples, such as from a biopsy, can include both tumor and normal cells. Further, a somatic mutation can occur on one of the two alleles for a gene, resulting in the somatic mutation being identified at a low frequency in the sample.

At 308, variants can be identified for the second sample. In exemplary embodiments, the algorithms for identifying variants in the second sample can be used to identify variants with a low stringency, so that a listing of variants for the second sample includes even variants with limited evidence.

At 310, a variant is selected from the list of variants identified for the first sample, and, at 312, the list of variants identified for the second sample is searched for the selected variant. At 314, a determination is made as to whether the variant was identified in the second sample.

When the variant was identified in the second sample, at 316, a likelihood the variant is found due to a sequencing error is determined. At 318, a determination can be made if the variant was likely identified due to sequencing error.

At 320, when it is unlikely the variant was identified due to sequencing errors, the variant can be considered as occurring throughout the organism and not specific to the tissue of the first sample, and thus may not be identified as a somatic mutation. For example, when the proportion of reads containing the variant from the second sample exceeds an expected error rate, the variant can be considered as a non-somatic mutation.

Alternatively, at 322, when the variant is likely identified based on a sequencing error, a determination can be made if there is sufficient coverage of the position in the sequencing information from both samples. For example, when the proportion of reads containing the variant from the second sample is less than an expected error rate, the presence of the variant reads can be considered due to sequencing error.

When there is sufficient coverage of the position in both samples, such as when a number of reads covering the position in each sample exceeds a threshold, the variant can be identified as a somatic variant, as shown at 324.

Alternatively, at 326, when there is not sufficient coverage of the position in either the sequencing information from the first sample or the sequencing information from the second sample, the variant can be identified as a low confidence somatic variant. That is, the variant may be a somatic variant, but there is insufficient evidence to have a high degree of confidence that the variant is present in the first sample but not in the second sample.

Returning to 314, when the selected variant is not found in the sequence information from the second sample, a determination can be made as to the amount of coverage of the position in the sequencing information from the second sample, as shown at 328.

When there is no coverage of the position, such as when the number of reads including the position is below a threshold, the variant can be identified as a low confidence somatic variant, as shown at 326.

Alternatively, when there is coverage of the position in the sequencing information for the second sample, a determination of the coverage in both samples can be made at 322.

In various embodiments, a somatic call quality value can be determined for variants identified as either somatic variants or low confidence somatic variants. The somatic call quality value can be indicative of the relative confidence that the variant is present in the first sample and not present in the second sample. For example, variants called as somatic variants can be assigned a somatic call quality value that is higher than for low confidence somatic variants. In various embodiments, the somatic call confidence value may be calculated based on the probability that a variant identified in the first sample is a true variant (PT) and the probability that a variant identified in the second sample is a true variant (PN). For example, the somatic call confidence value (QVs) can be calculated as $$QV_S = \frac{P_T(1 - P_N)}{P_T + P_N}.$$

The somatic call confidence value can be useful in focusing attention on variants with the highest probability of being true somatic mutations.

Figure 4:
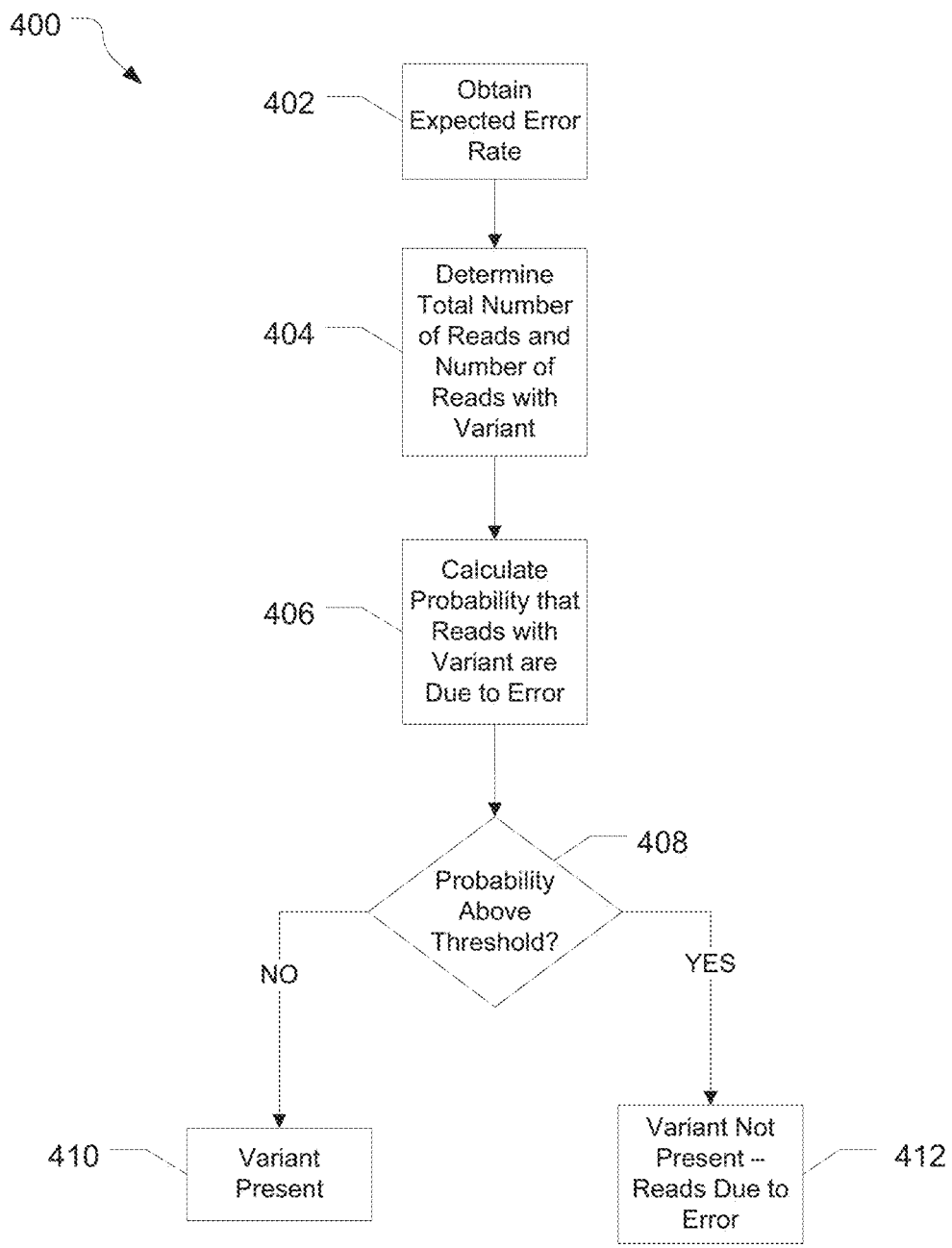
FIG. 4 is a flow diagram illustrating an exemplary method of determining if a variant is found due to a sequencing error.

FIG. 4 is an exemplary flow diagram illustrating a method of determining the likelihood a variant is found due to a sequencing error.

At 402, an expected error rate can be obtained. The expected error rate can be the rate at which a base can be expected to be miscalled, such as called an A rather than a T. In various embodiments, the expected error rate can be a constant rate across all positions. In various embodiments, the expected error rate can depend on the type of variant and the sequence context. For example, depending on the sequencing technique used, the error rate for an insertion or deletion following a homopolymer region can be greater than the error rate for a single base change.

At 404, the total number of reads covering a position and the number of reads showing the variant can be determined.

At 406, a probability that the number of reads showing the variant is due to a sequencing error can be calculated. For example, given an error rate of 2% and 100 reads covering a position, we would expect to see on average two reads with errors. Assuming there are six reads showing a variant, a binomial probability of those six reads resulting from a sequencing error would be approximately 1%.

In various embodiments, the probability that the number of reads showing the variant is due to a sequencing error can also be based upon a purity of the sample. For example, samples with a high purity may more closely be modeled by the binomial probability, whereas samples with a lower purity may be modeled using a modified probability to account for reads that result from contamination in the sample.

At 408, a determination can be made if the probability is above a threshold. At 410, when the probability is below a threshold, there is sufficient evidence that the variant is present in the sample. Alternatively, at 412, when the probability is above a threshold, it is likely that the variant was identified due to a sequencing error.

Figure 5:
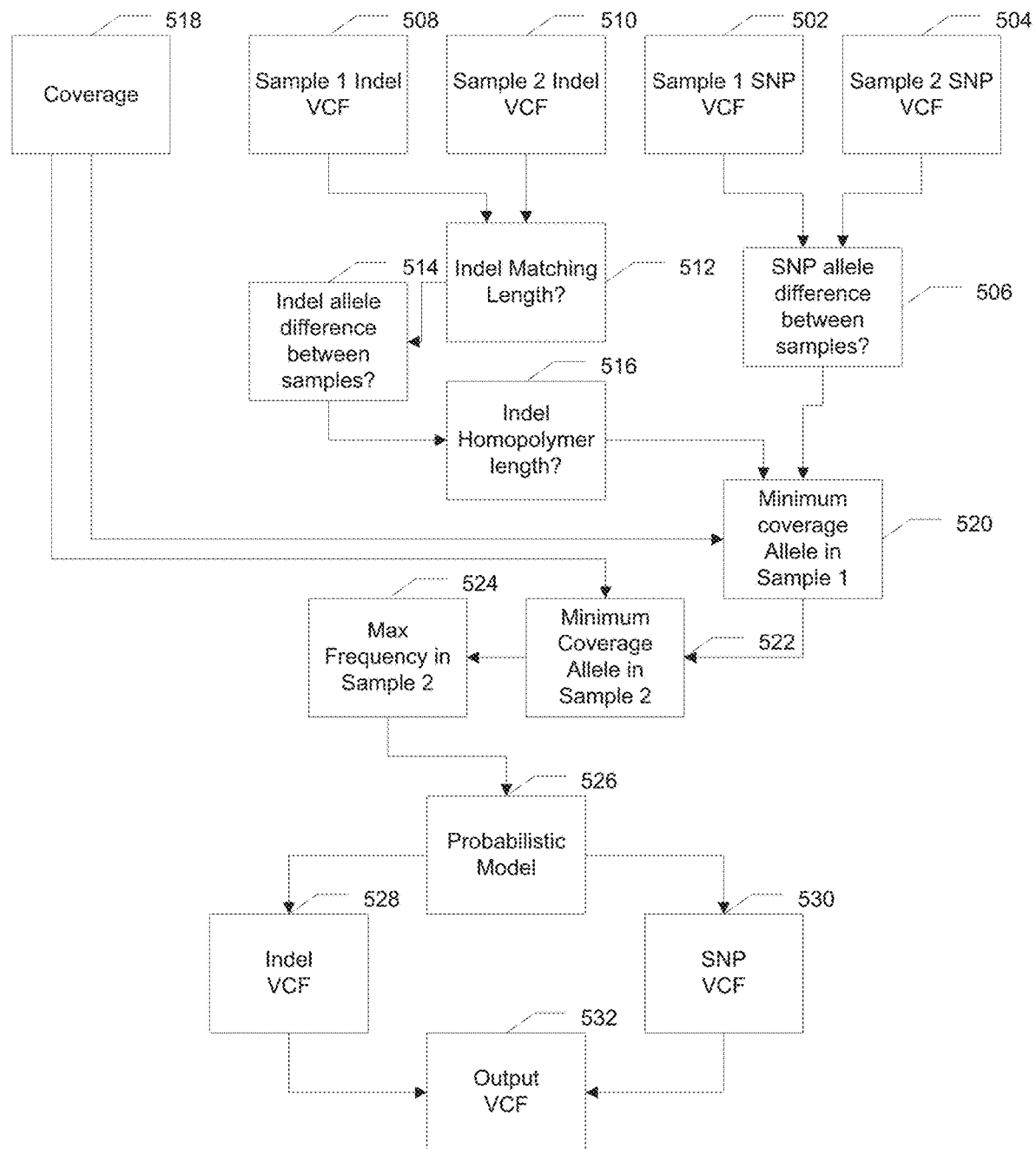
FIG. 5 is a diagram illustrating an exemplary data flow during a method of identifying somatic mutations, in accordance with various embodiments.

FIG. 5 is a diagram illustrating the data flow while comparing variants between two samples, in accordance with various embodiments. A listing of single nucleotide polymorphisms for the first and second samples, 502 and 504 respectively, are compared at 506 to identify differences between the samples. Additionally, a listing of indels for the first and second samples, 508 and 510 respectively, are compared at 512 to determine if the indel length matches between the first and second samples. At 514, for indels where the length matches, the indel sequence is compared. At 516, homopolymer length is compared between the samples.

Using the coverage 518 determined for both samples, for variants identified in Sample 1 that also have support from Sample 2, a check is made to determine if there is sufficient coverage at the position in Sample 1, as illustrated at 520. For those variants meeting the minimum coverage requirement in Sample 1, a check is made to determine if the is sufficient coverage of the position in Sample 2, as illustrated at 522. In various embodiments, the minimum coverage may be at least 5 reads spanning the position.

At 524, variants from Sample 1 that exceed a maximum frequency threshold in Sample 2 are considered to be present in both Sample 1 and Sample 2. In various embodiments, the maximum frequency threshold may be about 20, such that at least 20% of the reads spanning the position provide evidence to support the variant. For variants that have sufficient coverage in both Sample 1 and Sample 2, but do not meet the maximum frequency requirement, a probabilistic model 526 is used to determine if there is sufficient evidence in the reads of Sample 2 to support the variant call for Sample 2.

Based on the results of the probabilistic model, a list of indels 528 and a list of single nucleotide polymorphisms 530 that are present in Sample 1 but not supported by Sample 2 is generated. These lists are combined to provide the output list 532 of variants that are unique to Sample 1.

Figure 6:
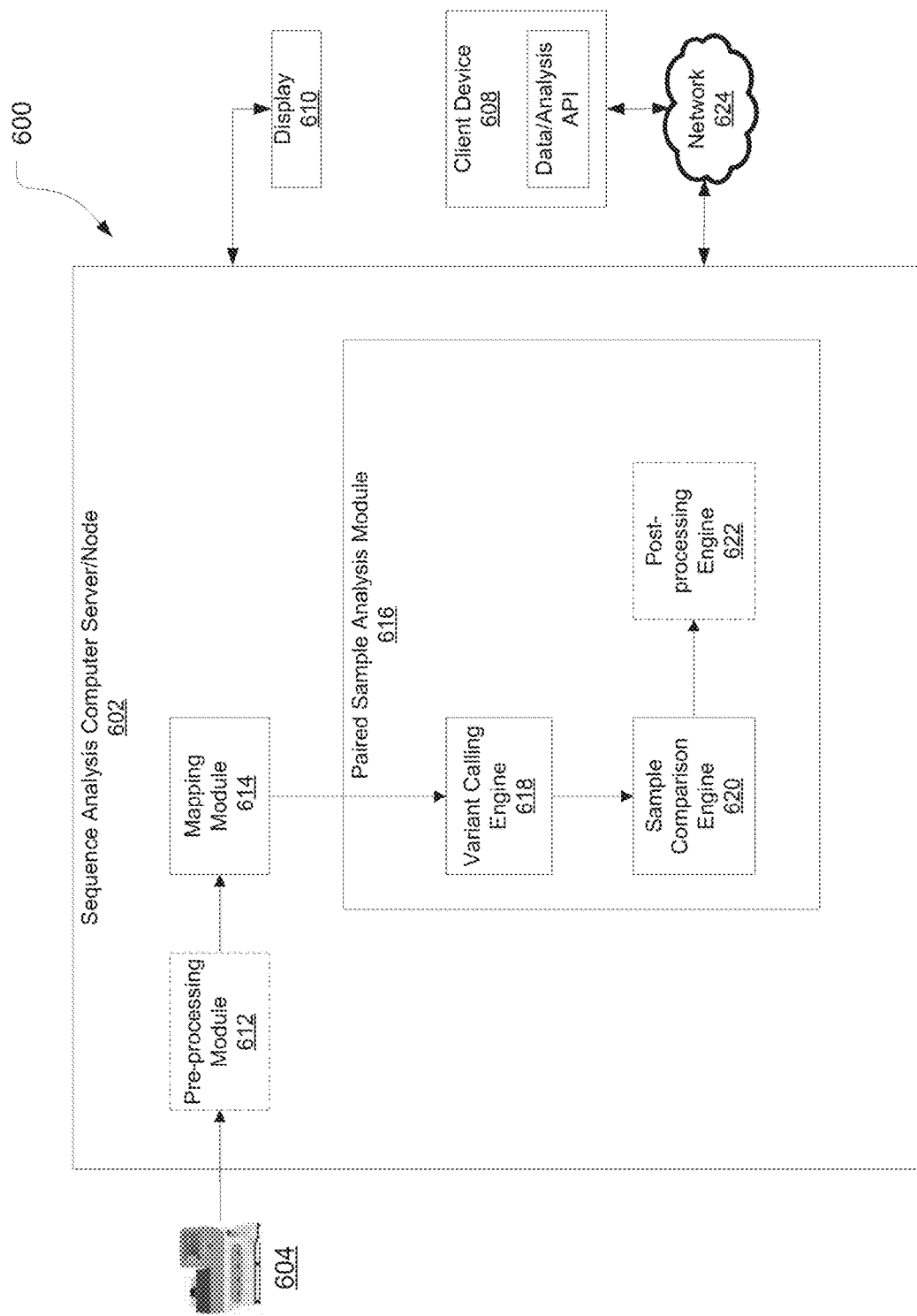
FIG. 6 is a schematic diagram of an exemplary genetic analysis system, in accordance with various embodiments.

FIG. 6 is a schematic diagram of a system for identifying variants, in accordance with various embodiments.

As depicted herein, variant analysis system 600 can include a nucleic acid sequence analysis device 604 (e.g., nucleic acid sequencer, real-time/digital/quantitative PCR instrument, microarray scanner, etc.), an analytics computing server/node/device 602, and a display 610 and/or a client device terminal 608.

In various embodiments, the analytics computing server/node/device 602 can be communicatively connected to the nucleic acid sequence analysis device 604, and client device terminal 608 via a network connection 624 that can be either a "hardwired" physical network connection (e.g., Internet, LAN, WAN, VPN, etc.) or a wireless network connection (e.g., Wi-Fi, WLAN, etc.).

In various embodiments, the analytics computing device/server/node 602 can be a workstation, mainframe computer, distributed computing node (such as, part of a "cloud computing" or distributed networking system), personal computer, mobile device, etc. In various embodiments, the nucleic acid sequence analysis device 604 can be a nucleic acid sequencer, real-time/digital/quantitative PCR instrument, microarray scanner, etc. It should be understood, however, that the nucleic acid sequence analysis device 604 can essentially be any type of instrument that can generate nucleic acid sequence data from samples obtained from an individual.

The analytics computing server/node/device 602 can be configured to host an optional pre-processing module 612, a mapping module 614, and a paired sample analysis module 616.

Pre-processing module 612 can be configured to receive from the nucleic acid sequence analysis device 604 and perform processing steps, such as conversion from f space to base space, color space to base space, or from flow space to base space, determining call quality values, preparing the read data for use by the mapping module 614, and the like.

The mapping module 614 can be configured to align (i.e., map) a nucleic acid sequence read to a reference sequence. Generally, the length of the sequence read is substantially less than the length of the reference sequence. In reference sequence mapping/alignment, sequence reads are assembled against an existing backbone sequence (e.g., reference sequence, etc.) to build a sequence that is similar but not necessarily identical to the backbone sequence. Once a backbone sequence is found for an organism, comparative sequencing or re-sequencing can be used to characterize the genetic diversity within the organism's species or between closely related species. In various embodiments, the reference sequence can be a whole/partial genome, whole/partial exome, etc.

In various embodiments, the sequence read and reference sequence can be represented as a sequence of nucleotide base symbols in base space. In various embodiments, the sequence read and reference sequence can be represented as one or more colors in color space. In various embodiments, the sequence read and reference sequence can be represented as nucleotide base symbols with signal or numerical quantitation components in flow space.

In various embodiments, the alignment of the sequence fragment and reference sequence can include a limited number of mismatches between the bases that comprise the sequence fragment and the bases that comprise the reference sequence. Generally, the sequence fragment can be aligned to a portion of the reference sequence in order to minimize the number of mismatches between the sequence fragment and the reference sequence.

The paired sample analysis module 616 can include a variant calling engine 618, a sample comparison engine 620, and an optional post processing engine 622. In various embodiments, variant calling module 616 can be in communications with the mapping module 614. That is, the variant calling module 616 can request and receive data and information (through, e.g., data streams, data files, text files, etc.) from mapping module 614. In various embodiments, the variant calling module 616 can be configured to communicate variants called for a sample genome as a *.vcf, *.gff, or *.hdf data file. It should be understood, however, that the called variants can be communicated using any file format as long as the called variant information can be parsed and/or extracted for later processing/analysis.

The variant calling engine 618 can be configured to receive mapped reads from the mapping module 614, analyze the alignments to detect and call (i.e., identify) one or more genomic variants within the reads, and provide variants to the sample comparison engine 620. Examples of genomic variants that can be called by a variant calling engine 618 include but are not limited to: single nucleotide polymorphisms (SNP), nucleotide insertions or deletions (indels), copy number variations (CNV) identification, inversion polymorphims, etc.

Sample comparison engine 620 can be configured to receive variants found in first and second samples from the variant calling engine 618, and determine if a variant found in reads from the first sample is also found in reads from the second sample. Additionally, the sample comparison engine 620 can determine a likelihood that a variant found in reads from the second sample are due to a sequencing error, and calculate a somatic call quality value indicative of the relative confidence that the variant is present in the first sample and not present in the second sample.

Post processing engine 622 can be configured to receive the somatic variants identified by the sample comparison engine 620 and perform additional processing steps, such as filtering variants, and formatting the variant data for display on display 610 or use by client device 608.

In various embodiments, the somatic variants can be annotated with functional or interpretive annotations, and a report can be generated to identify the somatic variants and provide the annotations, such as is described in more detail in U.S. patent application Ser. No. 13/648,998 titled "Systems and Methods for Analysis and Interpretiation of Nucleic Acid Sequence Data" filed Oct. 10, 2012 which is incorporated by reference in entirety).

Client device 608 can be a thin client or thick client computing device. In various embodiments, client terminal 608 can have a web browser (e.g., INTERNET EXPLORER™, FIREFOX™, SAFARI™, etc) that can be used to communicate information to and/or control the operation of the pre-processing module 612, mapping module 614, realignment engine 618, variant calling engine 620, and post processing engine 622 using a browser to control their function. For example, the client terminal 608 can be used to configure the operating parameters (e.g., match scoring parameters, annotations parameters, filtering parameters, data security and retention parameters, etc.) of the various modules, depending on the requirements of the particular application. Similarly, client terminal 608 can also be configure to display the results of the analysis performed by the variant calling module 616 and the nucleic acid sequencer 604.

It should be understood that the various data stores disclosed as part of system 600 can represent hardware-based storage devices (e.g., hard drive, flash memory, RAM, ROM, network attached storage, etc.) or instantiations of a database stored on a standalone or networked computing device(s).

It should also be appreciated that the various data stores and modules/engines shown as being part of the system 600 can be combined or collapsed into a single module/engine/data store, depending on the requirements of the particular application or system architecture. Moreover, in various embodiments, the system 600 can comprise additional modules, engines, components or data stores as needed by the particular application or system architecture.

In various embodiments, the system 600 can be configured to process the nucleic acid reads in color space. In various embodiments, system 600 can be configured to process the nucleic acid reads in base space. In various embodiments, system 600 can be configured to process the nucleic acid sequence reads in flow space. It should be understood, however, that the system 600 disclosed herein can process or analyze nucleic acid sequence data in any schema or format as long as the schema or format can convey the base identity and position of the nucleic acid sequence.

In various embodiments, the methods of the present teachings may be implemented in a software program and applications written in conventional programming languages such as C, C++, etc.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

The embodiments described herein, can be practiced with other computer system configurations including hand-held devices, microprocessor systems, microprocessor-based or programmable consumer electronics, minicomputers, mainframe computers and the like. The embodiments can also be practiced in distributing computing environments where tasks are performed by remote processing devices that are linked through a network.

It should also be understood that the embodiments described herein can employ various computer-implemented operations involving data stored in computer systems. These operations are those requiring physical manipulation of physical quantities. Usually, though not necessarily, these quantities take the form of electrical or magnetic signals capable of being stored, transferred, combined, compared, and otherwise manipulated. Further, the manipulations performed are often referred to in terms, such as producing, identifying, determining, or comparing.

Any of the operations that form part of the embodiments described herein are useful machine operations. The embodiments, described herein, also relate to a device or an apparatus for performing these operations. The systems and methods described herein can be specially constructed for the required purposes or it may be a general purpose computer selectively activated or configured by a computer program stored in the computer. In particular, various general purpose machines may be used with computer programs written in accordance with the teachings herein, or it may be more convenient to construct a more specialized apparatus to perform the required operations.

Certain embodiments can also be embodied as computer readable code on a computer readable medium. The computer readable medium is any data storage device that can store data, which can thereafter be read by a computer system. Examples of the computer readable medium include hard drives, network attached storage (NAS), read-only memory, random-access memory, CD-ROMs, CD-Rs, CD-RWs, magnetic tapes, and other optical and non-optical data storage devices. The computer readable medium can also be distributed over a network coupled computer systems so that the computer readable code is stored and executed in a distributed fashion.

What is claimed is:

1. A method of identifying a somatic mutation in nucleic acid sequence reads generated by a nucleic acid sequence analysis device, the method comprising:
receiving a first sequence information and a second sequence information at a processor, wherein the first sequence information represents the nucleic acid sequencing reads generated from a first sample in an NGS assay and the second sequence information represents the nucleic acid sequencing reads generated from a second sample in the NGS assay;
identifying a variant in the first sequence information;
determining if the variant is present in the second sequence information;
determining, when the variant is present in the second sequence information, whether the variant in the second sequence information is due to sequencing error;
determining first and second coverage levels of a position corresponding to the variant in the first and second sequence information;
and
identifying the variant as a somatic mutation when the variant in the second sequence information is due to sequencing error and the first and second coverage levels are above a coverage threshold.

2. The method of claim 1, further comprising identifying the variant as a somatic mutation when the variant is not present in the second sequence information and when the first and second coverage levels are not less than the coverage threshold.

3. The method of claim 1, further comprising identifying the variant as a low confidence somatic mutation when the variant is not present in the second sequence information and when the second coverage level is less than the coverage threshold.

4. The method of claim 1, further comprising identifying the variant as a low confidence somatic mutation when the first coverage level is less than the coverage threshold.

5. The method of claim 1, further comprising identifying the variant as a low confidence somatic mutation when the second coverage level is less than the coverage threshold.

6. The method of claim 1, wherein the variant identified in the first sequence information is a low frequency variant.

7. The method of claim 1, wherein the variant identified in the second sequence information has a low stringency.

8. The method of claim 1, further comprising determining a somatic call confidence value based on a probability that the variant identified in the first sequence information is a true variant and a probability that the variant identified in the second sequence information is a true variant.

9. The method of claim 1, wherein the first sample comprises a tumor sample and the second sample comprises a non-tumor sample.

10. A system for identifying a somatic mutation in nucleic acid sequence reads generated by a nucleic acid sequence analysis device, comprising:
a processor configured to:
receive a first sequence information and a second sequence information, wherein the first sequence information represents the nucleic acid sequencing reads generated from a first sample in an NGS assay and the second sequence information represents the nucleic acid sequencing reads generated from a second sample in the NGS assay;
identify a variant in the first sequence information;
determine if the variant is present in the second sequence information;
determine, when the variant is present in the second sequence information, whether the variant in the second sequence information is due to sequencing error;
determine first and second coverage levels of a position corresponding to the variant in the first and second sequence information; and
identify the variant as a somatic mutation when the variant in the second sequence information is due to sequencing error and the first and second coverage levels are above a coverage threshold.

11. The system of claim 10, wherein the first sample comprises a tumor sample and the second sample comprises a non-tumor sample.

12. The system of claim 10, wherein the processor is further configured to identify the variant as a somatic mutation when the variant is not present in the second sequence information and when the first and second coverage levels are not less than the coverage threshold.

13. The system of claim 10, wherein the processor is further configured to identify the variant as a low confidence somatic mutation when the variant is not present in the second sequence information and when the second coverage level is less than the coverage threshold.

14. The system of claim 10, wherein the processor is further configured to identify the variant as a low confidence somatic mutation when the first coverage level is less than the coverage threshold.

15. The system of claim 10, wherein the processor is further configured to identify the variant as a low confidence somatic mutation when the second coverage level is less than the coverage threshold.

16. The system of claim 10, wherein the variant identified in the first sequence information is a low frequency variant.

17. The system of claim 10, wherein the variant identified in the second sequence information has a low stringency.

18. The system of claim 10, wherein the processor is further configured to determine a somatic call confidence value based on a probability that the variant identified in the first sequence information is a true variant and a probability that the variant identified in the second sequence information is a true variant.

19. A method of identifying a somatic mutation, comprising:
attaching a first adapter including a barcode sequence to fragments of a first nucleic acid sample in an NGS assay;
attaching a second adapter including a barcode sequence to fragments of a second nucleic acid sample in the NGS assay;
sequencing the first and second nucleic acid samples substantially simultaneously to generate a plurality of reads, whereby sequencing the first and second nucleic acid samples substantially simultaneously reduces differences due to variations between separate sequencing runs;

classifying the reads corresponding to the first nucleic acid sample as a first sequence information based on the first barcode sequence;

classifying the reads corresponding to the second nucleic acid sample as a second sequence information based on the first and second barcode sequences;

identifying a variant in the first sequence information;

determining if the variant is present in the second sequence information;

calculating, when the variant is present in the second sequence information, a likelihood that the variant is present in the second sequence information above an expected error rate; and identifying the variant as a somatic mutation when the likelihood is below a threshold.

* * * * *